United States Patent
Hu et al.

(10) Patent No.: US 8,940,329 B2
(45) Date of Patent: Jan. 27, 2015

(54) HIGH IBUPROFEN CONTENT GRANULES AND THEIR PREPARATION AND THEIR USE IN PHARMACEUTICAL DOSAGE FORMS

(75) Inventors: Patrick C. Hu, Baton Rouge, LA (US); Gregory H. Lambeth, Baton Rouge, LA (US); Arcelio J. Malcolm, Baton Rouge, LA (US)

(73) Assignee: SI Group, Inc., Schenectady, NY (US)

( * ) Notice: Subject to any disclaimer, the term of this patent is extended or adjusted under 35 U.S.C. 154(b) by 1727 days.

(21) Appl. No.: 11/260,662

(22) Filed: Oct. 28, 2005

(65) Prior Publication Data

US 2006/0034919 A1   Feb. 16, 2006

Related U.S. Application Data

(63) Continuation-in-part of application No. PCT/US2005/016833, filed on May 13, 2005.

(60) Provisional application No. 60/583,839, filed on Jun. 30, 2004.

(51) Int. Cl.
  *A61K 9/20* (2006.01)
  *A01N 37/10* (2006.01)
  *A61K 31/19* (2006.01)
  *A61K 9/16* (2006.01)
  *A61K 31/192* (2006.01)

(52) U.S. Cl.
  CPC ............ *A61K 9/2077* (2013.01); *A61K 9/1652* (2013.01); *A61K 9/1688* (2013.01); *A61K 9/1694* (2013.01); *A61K 9/2059* (2013.01); *A61K 31/192* (2013.01)
  USPC .......................................... 424/464; 514/570

(58) Field of Classification Search
  None
  See application file for complete search history.

(56) References Cited

U.S. PATENT DOCUMENTS

| 4,609,675 | A | | 9/1986 | Franz | |
|---|---|---|---|---|---|
| 4,837,031 | A | | 6/1989 | Denton | |
| 4,904,477 | A | * | 2/1990 | Ho et al. | .................. 424/465 |
| 4,911,921 | A | | 3/1990 | Denton et al. | |
| 5,104,648 | A | | 4/1992 | Denton et al. | |
| 5,320,855 | A | * | 6/1994 | Roche et al. | .................. 424/495 |
| 5,725,883 | A | * | 3/1998 | Staniforth et al. | ............ 424/489 |
| 6,348,216 | B1 | | 2/2002 | Kushla et al. | |
| 6,361,794 | B1 | | 3/2002 | Kushla et al. | |
| 6,599,531 | B2 | | 7/2003 | Kushla et al. | |
| 2002/0119193 | A1 | * | 8/2002 | Le et al. | .................. 424/465 |

FOREIGN PATENT DOCUMENTS

| EP | 0 298 666 | | 1/1989 | |
|---|---|---|---|---|
| WO | WO 88/08299 | | 11/1988 | |
| WO | WO94/10993 | * | 5/1994 | ............ A61K 31/19 |
| WO | 0217855 A2 | | 3/2002 | |
| WO | WO 02/083119 | | 10/2002 | |
| WO | WO 2005/030166 | | 4/2005 | |

* cited by examiner

*Primary Examiner* — Trevor Love
(74) *Attorney, Agent, or Firm* — Jeffrey N. Townes; LeClairRyan

(57) ABSTRACT

Described are granules composed at least of a substantial amount of ibuprofen, at least one pharmaceutically-acceptable super disintegrant, and at least one pharmaceutically-acceptable binder different from the super disintegrant(s), the super disintegrant(s) being substantially uniformly dispersed throughout the granules. The methods for preparing such granules are described. The granules are useful in forming solid dosage forms such as filled capsules or compressed solid dosage forms.

23 Claims, No Drawings

HIGH IBUPROFEN CONTENT GRANULES AND THEIR PREPARATION AND THEIR USE IN PHARMACEUTICAL DOSAGE FORMS

REFERENCE TO RELATED APPLICATION

This application is a continuation-in-part of commonly-owned International Application No. PCT/US05/16833, filed May 13, 2005, which international application claims benefit and priority of Appln. No. 60/583,839, filed Jun. 30, 2004.

TECHNICAL FIELD

This invention relates to new pharmaceutical granules with high ibuprofen drug content, their preparation, and their use in the formulation or preparation of a variety of dosage forms such as compressed tablets and filled capsules.

BACKGROUND

A need exists for an effective way of providing granules containing high concentrations of ibuprofen which can be rapidly dissolved in water and which can form solid dosage forms which likewise can be dissolved rapidly in water.

SUMMARY OF THE INVENTION

It has now been found that the foregoing need can be fulfilled by forming granular ibuprofen compositions comprising ibuprofen, at least one pharmaceutically-acceptable super disintegrant, and at least one pharmaceutically-acceptable binder, which binder is different from said super disintegrant, wherein said composition is in the form of granules in which said super disintegrant is substantially uniformly dispersed. The use of a binder which is different from the super disintegrant ensures that the substantially uniformly dispersed super disintegrant will remain substantially uniformly dispersed. By binding the substantially uniformly dispersed super disintegrant in place, the granules will rapidly dissolve upon contact with water. In addition, use of a super disintegrant in the formation of solid dosage forms from the granules of this invention, results in the formation of solid dosage forms which themselves rapidly dissolve in water to form an aqueous solution of the pharmaceutical composition.

In preferred embodiments the granules of this invention additionally contain a small amount of a pharmaceutically-acceptable wetting agent.

The granules of this invention contain at least about 75 wt % and preferably at least about 85 wt % of ibuprofen on a dry weight basis. Preferably the granules of this invention contain up to about 95 wt % of ibuprofen on a dry weight basis.

It has also been found that when preparing the granules of this invention, the inclusion of very small amounts of fumed silica greatly enhances the flowability of the granules and decreases the attrition of the granules during processing and handling. Another feature of this invention is that the granules of the invention can be readily compounded with (i) other pharmaceutically-acceptable excipients such as one or more lubricants, glidants, fillers, surfactants or wetting agents, additional disintegrant(s), additional binders and the like, and/or (ii) other active pharmaceutical ingredients such as pseudoephedrine, hydrocodone, oxycodone, diphenhydramine, and the like.

To prepare granules of this invention, a process of this invention comprises:

a) forming a mixture from, or obtaining a mixture of, finely-divided ibuprofen and at least one finely-divided pharmaceutically-acceptable super disintegrant;
b) fluidizing mixture from a) with gaseous fluidizing agent to thereby form a substantially homogeneous dry mixture comprised of ibuprofen and at least one super disintegrant;
c) while fluidizing homogeneous dry mixture formed in b) with heated gaseous fluidizing agent, spraying onto the fluidized mixture an aqueous solution, dispersion, or suspension of at least one pharmaceutically-acceptable binder which binder is different from said super disintegrant, to form wet granules comprised of ibuprofen, at least one pharmaceutically-acceptable super disintegrant, and at least one pharmaceutically-acceptable binder which is different from the at least one pharmaceutically-acceptable super disintegrant; and
d) fluidizing (preferably continuously fluidizing) wet granules from c) with heated gaseous fluidizing agent so as to produce dried granules having a moisture content of less than 5 wt % (preferably less than 2 wt %) based on the weight of the granules.

Preferably the respective amounts of the finely-divided ibuprofen, the at least one finely-divided pharmaceutically-acceptable super disintegrant used, and the at least one pharmaceutically-acceptable binder used are such as to provide granules containing (i) in the range of about 85 to about 95 wt % of ibuprofen based on the dry weight of the granules, (ii) in range of about 0.5 to about 10 wt % (preferably in the range of about 1 to about 5 wt %) of the at least one super disintegrant based on the dry weight of the granules, and (iii) in the range of about 2 to about 14.5 wt % (preferably in the range of about 5 to about 10 wt %) of at least one binder based on the dry weight of the granules.

When preparing granules of this invention containing a wetting agent (i.e., at least one wetting agent), a process as above is used wherein c) is conducted by spraying onto the fluidized mixture either separately and/or in combination (i) such aqueous solution, dispersion, or suspension of at least one pharmaceutically-acceptable binder and (ii) an aqueous solution, dispersion, or suspension of at least one pharmaceutically-acceptable wetting agent, to form wet granules; and wherein the respective amounts of the components used produce granules which additionally contain in the range of about 0.01 to about 2.0 wt % (preferably in the range of 0.01 to about 0.2 wt %) of said at least one pharmaceutically-acceptable wetting agent based on the dry weight of the granules.

As used anywhere herein, the term "finely-divided" means that the particles are small enough to be fluidized by a gaseous fluidizing agent such as dry air when practicing the process of this invention. There is no mathematically precise, hard and fast dividing line between finely-divided and non-finely-divided for fluidizing purposes as the density of the substance of which the particles are composed and the rate of gaseous flow used in the fluidization will affect the capability of the particles to be fluidized. Thus one should consider what one of ordinary skill in the art of fluidization would consider "finely-divided". Certainly most powdery or microsized materials of the types involved here are finely-divided. In any doubtful case a simple laboratory fluidization test under relevant operating conditions (e.g., gas composition, gas velocity, gas temperature) will enable determination as to whether a given substance or mixture of substances is "finely-divided" within the meaning of this disclosure.

Other embodiments, features and advantages of this invention will be still further apparent from the ensuing description and appended claims.

FURTHER DETAILED DESCRIPTION OF THE INVENTION

As noted above, the granules of this invention require the presence of ibuprofen, at least one pharmaceutically-acceptable super disintegrant, and at least one pharmaceutically-acceptable binder which is a different chemical substance from the super disintegrant. Preferably, the granules also contain a pharmaceutically-acceptable wetting agent. The granules of this invention typically contain in the range of about 85 to about 95 wt % of ibuprofen based on the total dry weight of the granules. Preferred granules of this invention contain in the range of about 88 to about 92 wt % of ibuprofen based on the total dry weight of the granules.

Pharmaceutically-Acceptable Super Disintegrants

A super disintegrant is a disintegrant that swells in water to increase in volume by about 200% or more. Among suitable super disintegrants that can be used in forming the granules of this invention are such substances as croscarmellose sodium, crospovidone, and sodium starch glycolate. Preferred super disintegrants are croscarmellose sodium and sodium starch glycolate, with sodium starch glycolate being particularly preferred. In forming the granules of this invention, one or more such super disintegrants are employed typically in an amount in the range of about 0.5 to about 10 wt %, and preferably in the range of about 1 to about 5 wt % based on the total dry weight of the granules. However, when using croscarmellose sodium an amount in the range of 0.5 to about 3 wt % and preferably in the range of about 0.5 to about 2 wt % is all that is required, and use of this super disintegrant in such small amounts is advantageous in view of the relatively high cost of croscarmellose sodium. In contrast, sodium starch glycolate is substantially less costly and although it is very effective at similar low dosage levels, it can be employed at higher concentrations because of its lower cost as compared to croscarmellose sodium.

Pharmaceutically-Acceptable Binders

The binder used in the present granules can be selected from those known in the art to be suitable for use in directly compressible pharmaceutical formulations. Among suitable examples of such binders are starches, celluloses, and sugars. More specifically the binder may be pregelatinized starch, microcrystalline cellulose, lactose, corn starch, hydroxypropylmethylcellulose, hydroxypropylcellulose, ethylcellulose, gelatin, corn sweetener, acacia, sodium alganate, carboxymethylcellulose, waxes, and the like. Starch and pregelatinized starch are preferred binders. In forming the granules of this invention, one or more such binders are employed typically in an amount in the range of about 2 to about 14.5 wt %, and preferably in the range of about 5 to about 10 wt % based on the total dry weight of the granules.

Pharmaceutically-Acceptable Wetting Agents

In preferred embodiments of the invention at least one pharmaceutically-acceptable wetting agent is used in the preparation of, and is present in, the granules of this invention. Among suitable wetting agents for such use are included polyoxyethylene sorbitan monooleate, sodium lauryl sulfate, polyethoxylated castor oil, polyethoxylated hydrogenated castor oil, and the like. Commercially available wetting agents which can be used include products known under such trade designations as Cremophor, Myrj, Polyoxyl 40 stearate, Emerest 2675, Lipal 395, and PEG 3350. Preferred wetting agents are polyoxyethylene sorbitan fatty acid esters such as polyoxyethylene sorbitan monooleate, especially Polysorbate 80 which is available in the marketplace from various suppliers and which is referred to chemically as polyoxyethylene 20-sorbitan monooleate (CAS 9005-65-6). In forming the preferred granules of this invention, one or more such wetting agents are employed typically in an amount in the range of about 0.01 to about 2.0 wt % and preferably in the range about 0.01 to about 0.2 wt %, both ranges based on the total dry weight of the granules. Use of polysorbate 80 in an amount in the range of about 0.01 to about 0.2 wt % (especially in an amount of about 0.02 wt %) based on the total dry weight of the granules constitutes a preferred embodiment. For wetting agents that are less effective than polysorbate 80, amounts in the range of about 0.05 to about 0.2 wt % based on the total dry weight of the granules is recommended.

Pharmaceutically-Acceptable Glidants

In preferred embodiments of the invention at least one pharmaceutically-acceptable glidant is used in the preparation of, and is present in, the granules of this invention. Non-limiting examples of such glidants are finely-divided (i.e., powdery) materials such as talc, silica, corn starch, microcrystalline cellulose, stearic acid, and non-toxic metal stearate, or mixtures of materials of this type. Powdery (microfine) siliceous materials such as talc, precipitated silica and fumed silica are preferred. Fumed silica is more preferred. Generally speaking the amount of glidant used, when used, is in the range of about 0.01 to about 0.5 wt %, desirably in the range of about 0.01 to about 0.1 wt %, and in the case of glidants not as efficient as fumed silica, desirably in the range of about 0.02 to about 0.5 wt %, each based on the weight of the final glidant treated product. While fumed silica is very effective when used in amounts in the range of about 0.02 to about 0.1 wt % based on the weight of the final fumed silica treated product, it is preferred to use an amount of fumed silica in the range of about 0.01 to about 0.05 wt % based on the weight of the final fumed silica treated product, such as about 0.02 wt % based on the weight of the final fumed silica treated product.

By "dry weight" of the granules of this invention is meant the weight of the granules reduced by the weight of water therein as determined by Karl Fischer titration. In other words, from the weights of the granules is deducted the weight of water present therein as determined by Karl Fischer titration performed on such granules.

Thus, to determine the weight percentage of ibuprofen based on the total dry weight of the granules, two determinations are required. First, a given batch of the granules is subjected to an assay determination by HPLC in order to determine the apparent percentage of ibuprofen in the granules. Then, a Karl Fischer titration is conducted on the same batch of granules to determine the water content of the granules. Then, the apparent weight of the ibuprofen in the granules is arithmetically adjusted by taking into consideration of the weight of the water in the granules. For example, if a batch of granules of this invention when subjected to assay determination by HPLC indicates the presence of say 90.0 wt % of ibuprofen and if upon Karl Fischer titration the same batch of granules at substantially the same time has a water content of say 2 wt %, then the percentage of ibuprofen in the granules on a dry weight basis is 90.0/(100%−2%) or 91.8 wt %.

By "dry weight" as applied to the components of the granules of this invention other than ibuprofen is meant the target weight percentage of that component other than ibuprofen based on the weight of the component corrected for its water content, if any, used in the preparation of the granules. For example, if the super disintegrant used was known to contain 3 wt % of water, e.g., by Karl Fischer titration, then to correct such water content, the amount of that disintegrant used would be increased to 1/0.97 or 1.03. Thus for the purposes of this invention the dry weight in this case is the corrected target weight of that component.

Preparation of the Granules

In order to effectively produce the granules of this invention, it is desirable to employ a preferred fluidized bed granulation method of this invention. This method when not employing a wetting agent in forming the granules, comprises the following steps:

a) forming a mixture from, or obtaining a mixture of, finely-divided ibuprofen and at least one finely-divided pharmaceutically-acceptable super disintegrant;

b) fluidizing mixture from a) using a gaseous fluidizing agent such as air to thereby form a substantially homogeneous dry mixture;

c) while fluidizing homogeneous dry mixture formed in b) with heated gaseous fluidizing agent such as dehumidified air, spraying onto the fluidized mixture an aqueous solution, dispersion, or suspension of at least one pharmaceutically-acceptable binder to form wet granules; and d) continuously fluidizing wet granules from c) with heated gaseous fluidizing agent such as dehumidified air so as to produce granules having a moisture content of less than 5 wt %, and more preferably less than 2 wt %;

the respective amounts of the finely-divided ibuprofen, the at least one finely-divided pharmaceutically-acceptable super disintegrant used, and the at least one pharmaceutically-acceptable binder used are such as to provide a mixture containing (i) in the range of about 85 to about 95 wt % of ibuprofen, (ii) in range of about 0.5 to about 10 wt %, and more preferably in the range of about 1 to about 5 wt % of the at least one super disintegrant, and (iii) in the range of about 2 to about 14.5 wt %, and more preferably in the range of about 5 to about 10 wt % of the at least one binder, the foregoing weight percentages each being based on the dry weight of the granules.

In b), c), and d) above, respectively, any gaseous fluidizing agent that is inert to the respective components that are present in the mixtures in b), in c), and in the wet and dry granules in d), and that will not prevent the formation of dry granules in d), can be used. Some non-limiting examples of gaseous fluidizing agents that can be used include, air, nitrogen, oxygen, argon, krypton, neon, and air enriched in nitrogen or other such inert gas or mixture of such gases. In at least c) and d), and desirably in b) also, the gaseous fluidizing agent should be dry so as to promote evaporation and drying of the fluidized solids present during the respective operations of b), c), and c). A preferred gaseous fluidizing agent on a cost effectiveness basis is dehumidified air. While two or three different kinds of gaseous fluidizing agents can be used in conducting b), c), and d), respectively, use of the same kind of gaseous fluidizing agent in b), c), and d) is deemed desirable as it simplifies the overall operation.

The temperature(s) of the heated inlet gaseous fluidizing agent such as dehumidified air used in conducting the above process can vary within reasonable limits. Typically such inlet gas (e.g., air) temperature in the respective fluidizing steps b), c) and d), will be at a temperature in the range of about 20 to about 80° C. and preferably in the range of about 50 to about 80° C. and more preferably in the range of about 60 to about 75° C. During the conduct of one or more of these respective fluidizing steps, the inlet gas (e.g., air) temperature can be increased or decreased, or both, as long as it remains substantially within the foregoing ranges. Also, the inlet gas (e.g., air) temperature(s) selected for use in conducting any given fluidizing step can be different from the temperature(s) used in conducting one or more of the other fluidizing steps. In other words, the inlet gas (e.g., air) temperatures used for the fluidizing steps are independent of each other and thus can all be the same or can involve one or more differences. Preferably, in conducting step c) the inlet gas temperature is selected so as to maintain a fluidized bed moisture content in the range of about 12 to about 20 wt %. Accordingly it is desirable in carrying out step c) to continuously monitor the moisture content of the granules in the fluidized bed, to continuously monitor the temperature of the inlet gas (e.g., air), and to adjust the temperature of the inlet gas (e.g., air) as needed so as to maintain the moisture content of the granules of the fluidized bed in the desirable range of about 12 to about 20 wt %. By maintaining the moisture content of the granules in this desirable range for a period of at least about 20 minutes, and preferably for at least about 30 minutes, the strength properties of the resultant granules is increased and the amount of fines is reduced. The temperature at which the mixture in step a) is formed is not critical so long as the ibuprofen is not heated to a temperature above about 75° C. long enough for melting or thermal degradation to occur.

Reference anywhere in this disclosure including the claims to moisture content of granules of the fluidized bed relates to the average moisture content of the granules as determined by removing a 20-gram sample from a sampling spout inserted into the fluidized bed while it is in a fluidized condition. From this 20-gram sample are randomly removed two 0.5 gram samples for analysis. These latter samples are subjected to Karl Fischer titration and the values obtained are averaged together.

To prepare the preferred granules of this invention containing a small amount of a wetting agent, the following fluidized bed granulation method of this invention is preferably employed. Because of the inclusion of one or more wetting agents, this preferred method comprises the following steps:

a) forming a mixture from, or obtaining a mixture of, finely-divided ibuprofen and at least one finely-divided pharmaceutically-acceptable super disintegrant;

b) fluidizing mixture from a) using a gaseous fluidizing agent such as air to thereby form a substantially homogeneous dry mixture;

c) while fluidizing homogeneous dry mixture formed in b) with heated gaseous fluidizing agent such as dehumidified air, spraying onto the fluidized mixture either separately and/or in combination (i) an aqueous solution, dispersion, or suspension of at least one pharmaceutically-acceptable binder and (ii) an aqueous solution, dispersion, or suspension of at least one pharmaceutically-acceptable wetting agent, to form wet granules;

d) continuously fluidizing wet granules from c) with heated gaseous fluidizing agent such as dehumidified air so as to produce granules having a moisture content of less than 5 wt %, and preferably less than 2 wt %;

the respective amounts of the finely-divided ibuprofen, the at least one finely-divided pharmaceutically-acceptable super disintegrant used, and the at least one pharmaceutically-acceptable binder used are such as to provide a mixture containing (i) in the range of about 85 to about 95 wt % of ibuprofen, (ii) in range of about 0.5 to about 10 wt %, and preferably in the range of about 1 to about 5 wt % of the at least one super disintegrant, (iii) in the range of about 2 to about 14.5 wt %, and preferably in the range of about 5 to about 10 wt % of the at least one binder, and (iv) in the range of about 0.01 to about 2.0 wt %, and preferably in the range of about 0.01 to about 0.2 wt % of at least one wetting agent, the foregoing weight percentages each being based on the dry weight of the granules. In conducting step c) of the above method, it is preferred to spray a solution, dispersion, or suspension of at least one pharmaceutically-acceptable binder followed by spraying at least one pharmaceutically-acceptable wetting agent onto the granules. In this way, the wetting agent tends to remain on the outer surface of the granules which aids in dissolution of the granules in water.

In b), c), and d), respectively, of the above fluidized bed granulation method involving use of a wetting agent, any gaseous fluidizing agent that is inert to the respective components that are present in the mixtures in b), in c), and in the wet and dry granules in d), and that will not prevent the formation of dry granules in d), can be used. Some non-limiting examples of gaseous fluidizing agents that can be used include, air, nitrogen, oxygen, argon, krypton, neon, and air enriched in nitrogen or other such inert gas or mixture of such gases. In at least c) and d), and desirably in b) also, the gaseous fluidizing agent should be dry so as to promote evaporation and drying of the fluidized solids present during the respective operations of b), c), and c). A preferred gaseous fluidizing agent on a cost effectiveness basis is dehumidified air. While two or three different kinds of gaseous fluidizing agents can be used in conducting b), c), and d), respectively, use of the same kind of gaseous fluidizing agent in b), c), and d) is deemed desirable as it simplifies the overall operation.

The temperatures of the heated inlet gaseous fluidizing agent such as dehumidified air used in conducting the above process in which a wetting agent is used, can also vary within reasonable limits. Typically such inlet gas (e.g., air) temperature in the respective fluidizing steps b), c), and d) will be at a temperature in the range of about 20 to about 80° C. and preferably in the range of about 50 to about 80° C. and more preferably in the range of about 60 to about 75° C. During the conduct of one or more of these respective fluidizing steps, the inlet gas (e.g., air) temperature can be increased or decreased, or both, as long as it remains substantially within the foregoing ranges. Also, the inlet gas (e.g., air) temperature(s) selected for use in conducting any given fluidizing step can be different from the temperature(s) used in conducting one or more of the other fluidizing steps. In other words, the inlet gas (e.g., air) temperatures used for the fluidizing steps are independent of each other and thus can all be the same or can involve one or more differences. Preferably, in conducting steps c) and d), the inlet gas (e.g., air) temperature is selected so as to maintain a fluidized bed moisture content in the range of about 12 to about 20 wt %. Accordingly it is desirable in carrying out steps c) and d) to continuously monitor the moisture content of the granules in the fluidized bed, to continuously monitor the temperature of the inlet gas (e.g., air), and to adjust the temperature of the inlet gas (e.g., air) as needed so as to maintain the moisture content of the granules of the fluidized bed in the desirable range of about 12 to about 20 wt %. By maintaining the moisture content of the granules in this desirable range for a period of at least about 20 minutes, and preferably for at least about 30 minutes, the strength properties of the resultant granules is increased and the amount of fines is reduced. Times in excess of about 60 minutes provide no significant additional benefit. Experience to date has indicated that granules having the greatest strength and lowest content of fines are formed by keeping the moisture content of the granules in the fluidized bed in the range of about 17 to about 20 wt % for periods of time in the range of about 30 to about 60 minutes. The temperature at which the mixture in step a) is formed is not critical so long as the ibuprofen is not heated to a temperature above about 75° C. long enough for thermal degradation to occur.

It should be noted that in conducting the processes of this invention with or without inclusion of a wetting agent, momentary increases in the inlet air temperature above about 80° C. can be tolerated and are within the scope of this invention provided that the time interval at such higher inlet air temperature is short enough as to result in no appreciable melting or appreciable thermal degradation of the ibuprofen. Likewise, decreases of temperature to below about 20° C. will usually cause no harm, but will increase the length of time required to conduct the given operation involving use of dry dehumidified air.

Optionally, the granules produced as described above, whether with or without a wetting agent, are subjected to sieving in order to remove larger and smaller particles than desired. Typically, the granules of this invention after sieving will pass through a U.S. Standard No. 16 mesh sieve and be retained on a U.S. Standard No. 200 mesh sieve. Preferred granules of this invention will pass through a U.S. Standard No. 20 mesh sieve and be retained on a U.S. Standard No. 150 mesh sieve.

This invention also provides a method of (i) improving the flowability of the granules of this invention, or (ii) reducing attrition of the granules during subsequent handling or blending operations, or (iii) bringing about both of (i) and (ii). Moreover, this method applies equally well to granules of this invention produced with a wetting agent or without a wetting agent. The method for accomplishing these objectives involves adding a glidant, i.e., at least one finely-divided (i.e., powdery) glidant, such as fumed silica, precipitated silica, or talc to the granules formed as above and blending the resultant mixture, preferably by use of a physical mixing procedure which does not appreciably break down the structure of the granules. Preferred apparatus for conducting such mixing procedure is a tumbling blender, such as a double cone blender, a V-shaped blender, or the like. Generally speaking the amount of glidant such as fumed silica used is in the range of about 0.01 to about 0.5 wt %, desirably in the range of about 0.01 to about 0.1 wt %, and in the case of glidants not as efficient as fumed silica, desirably in the range of about 0.02 to about 0.5 wt % each based on the weight of the final glidant treated product. While fumed silica is very effective when used in amounts in the range of about 0.02 to about 0.1 wt % based on the weight of the final fumed silica treated product, it is preferred to use an amount of fumed silica in the range of about 0.01 to about 0.05 wt % based on the weight of the final fumed silica treated product, such as about 0.02 wt % based on the weight of the final fumed silica treated product. In conducting this operation, the times used for achieving the desired flowability improvement, if not previously known, can readily be determined by conducting the foregoing mixing procedure for a given period of time followed by determining the flowability of a sample of the mixed product, made from a known amount of added glidant, e.g., fumed silica. If the mixed product has not yet achieved the desired flowability, then the mixing is continued for an additional time and another sample is removed and subjected to flow measurement. Such a procedure can be repeated as many times as necessary to thereby establish the total time period to be used for that type of granule when used with that amount of glidant addition and using that type of mixing apparatus. If such operations do not result in the formation of a product with desirable flow, the foregoing procedure should then be repeated after addition of a known increased amount of glidant such as fumed silica to the granules.

Additional preferred embodiments of this invention involve use of powdery siliceous glidants such as talc, precipitated silica, and especially fumed silica, in the processes of this invention for producing the granules of this invention. The amount used is such that the finished granules contain such glidant in an amount in the range of about 0.01 to about 0.05 wt % based on the total dry weight of the granules.

A preferred procedure for use in preparing the granules of this invention involves use of a fluid bed granulator and a blender. A suitable type of fluid bed granulator such as GPCG or WSG manufactured by Glatt Air Techniques, Inc. is charged with ibuprofen, a super disintegrant, which most preferably is sodium starch glycolate, and optionally a small portion of binder, most preferably pregelatinized starch. When using pregelatinized starch as the binder, an amount of up to about 3 wt % thereof, and more preferably up to about 1 wt % thereof based on the total dry weight of the granules, may be added to the granulator. The materials are fluidized until thoroughly blended. An amount of the binder providing a total in the range of 7 to about 14 wt % (including the binder previously added) based on the total dry weight of the granules, is dispersed in water using a high shear mixer to form a slurry containing between about 5 to about 10 wt % pregelatinized starch. Preferably, the water dispersion has a concentration of about 8 wt % pregelatinized starch binder. While continuing fluidizing, the dispersion is then sprayed onto the fluidized bed of ibuprofen, sodium starch glycolate, and pregelatinized starch mixture at a rate sufficient to maintain the powder bed moisture in the range of between about 12 to about 22 wt % during a period of from about 10 minutes to about 60 minutes and preferably from about 20 minutes to about 50 minutes. In addition to the spraying rate, other operational variables such as inlet air temperature, air wet bulb temperature, and air flow rate are all factors that can be adjusted to maintain the desired moisture range and duration. Immediately upon completion of spraying the starch solution, a spray of wetting agent, preferably a polysorbate solution, is initiated. This spray should provide a total in the range of about 0.01 to about 2 wt % of wetting agent based on the total dry weight of the granules. After completing the spraying of the wetting agent, the fluid bed operation is continued until a moisture level of 2 wt % has been reached and then the operation of the granulator is terminated. The content of the granulator bowl is sieved through a siever/shaker (manufactured by Sweco, a Division of M-I L.L.C.) equipped with a 16 mesh screen. During the sieving stage, if necessary, a fine mesh screen, such as U.S. Standard 200 mesh screen may also be installed on the shaker to remove excessive fine particles. The sieved material is then transferred into a suitable-size blender followed by the addition of a glidant, preferably fumed silica, and mixture is then blended to form the finished granules.

It can be seen therefore, that this invention provides, inter alia, a pharmaceutical composition prepared by a process in which (i) ibuprofen and at least one pharmaceutically-acceptable super disintegrant are mixed together in a fluidized bed to form a mixture and (ii) a pharmaceutically-acceptable binder, which binder is different from said super disintegrant, is sprayed on said mixture to form granules that comprise ibuprofen, said at least one super disintegrant, and said at least one binder. Similarly, this invention provides, inter alia, a process for preparing a pharmaceutical composition, which process comprises (i) mixing together in a fluidized bed ibuprofen and at least one pharmaceutically-acceptable super disintegrant to form a mixture and (ii) spraying onto said mixture a pharmaceutically-acceptable binder, which binder is different from said super disintegrant, to form granules that comprise ibuprofen, said at least one super disintegrant, and said at least one binder.

A preferred granular pharmaceutical composition of this invention consists essentially of about 85 to 95 wt % of ibuprofen, about 1 to 5 wt % of at least one pharmaceutically-acceptable super disintegrant, about 5 to 10 wt % of at least one pharmaceutically-acceptable binder that differs chemically from said super disintegrant, and about 0.01 to 2.0 wt % of at least one pharmaceutically-acceptable wetting agent.

Also provided by this invention is a pharmaceutical composition derived from a wet granulation process and containing ibuprofen, at least one pharmaceutically-acceptable super disintegrant, and at least one pharmaceutically-acceptable binder. As noted above, such composition contains less than 5 wt %, and preferably less than 2 wt % water.

Uses of the Granules

The granules of this invention can be used in various dosage forms. In one such embodiment the granules are encased in capsules such as gelatin capsules. In other embodiments the granules are subjected to compression in order to produce solid dosage forms such as tablets, caplets, discs, lozenges, and the like.

Typically, the granules of this invention and the solid dosage forms of this invention made using the granules of this invention which contain one or more other active pharmaceutical ingredients will have an ibuprofen content of at least about 20 wt % on a dry weight basis. Preferred granules and solid dosage forms of this invention which contain one or more active pharmaceutical ingredients will have an ibuprofen content of at least about 50 wt % on a dry weight basis.

The granules of this invention can be used directly to fill capsules. Because of their excellent free-flowing characteristics such operations can be conducted very efficiently. Moreover, because of their characteristics, such as density and size distribution, the capsules can be readily filled to capacity with a minimum of voids.

Another use for the granules of this invention is in the preparation of tablets and other solid dosage forms. In preparing such dosage forms, the granules are typically blended with one or more additional pharmaceutically-acceptable excipients. Among suitable excipients are such materials as fillers, disintegrants, lubricants, glidants, binders, preservatives, and the like. A highly advantageous feature of this invention is that because of the overall composition and physical characteristics of the granules, the amounts of such additional excipients can be minimal. Although polyvinylpyrrolidone (PVP) is not used in the granules of this invention because of its tendency to form low melting eutectics when admixed with ibuprofen, PVP can be used in the formation of solid dosage forms that are formed without generation of sufficient heat to result in formation of a low melting eutectic. Because many tableting and other compression operations used in forming solid dosage forms tend to form considerable heat during compression, the use of PVP in forming tablets, caplets, discs, lozenges, or the like should be restricted to instances where the apparatus used in forming such solid dosage forms does not generate much heat during the compression operations.

Another use of the granules is in the production of pharmaceuticals based on a combination of ibuprofen with at least one other active pharmaceutical ingredient. The high ibuprofen content and limited number of excipients make the granules amenable to blending with other active ingredients. Examples of such active ingredients are antihistamines, decongestants, antitussives, and other analgesics, muscle relaxants, and the like.

The following examples illustrate the practice of this invention. They are not intended to limit and should not be construed as limiting the generic character of the present invention. In the Examples, hardness of solid dosage forms was measured using a Distek Tablet Hardness Tester, dissolution time of solid dosage forms was measured using the test method set forth in USP XXI employing a SR8Plus dissolution tester (Hanson Research). Friability of solid dosage forms was measured on a Distek Friabulator model DF-3 using 20 solid dose units.

EXAMPLE 1

Preparation of Granules of the Invention

A 300 kg batch of granules of this invention is prepared by charging to the bowl of a GPCG 300 fluid bed granulator (Glatt Air Techniques, Inc., Ramsey, N.J.) the following ingredients in the amounts specified: 270 kg of ibuprofen 40 micron grade (Albemarle Corporation), 6 kg of sodium starch glycolate (Explotab Low PH), and 2.88 kg of pregelatinized starch, Uni-Pure WG 220 (National Starch Co.). Prior to charging, the ibuprofen is passed through a Sweco siever equipped with a U.S. Standard 16 mesh screen in order to delump the product. After charging the foregoing ingredients into the bowl, the granulator is activated so that the contents of the bowl are agitated and mixed with an air stream flowing upwardly through the screened bottom of the bowl sufficient to fluidize the bowl mixture. A binder solution is formed by slurrying 21 kg of Uni-Pure WG 220 pregelatinized starch in 241.5 kg of water to form an 8 wt % solution. This solution is sprayed onto the fluidized bowl mixture at a rate in the range of 1 to 4 kg per minute. During this time, the rate of flow of inlet air to the bowl is maintained in the range of about 2000 to about 5000 cubic feet per minute, and the inlet air temperature is maintained in the range of about 50 to about 75° C. Upon completing the spraying of the starch solution, a spray of a solution of wetting agent is initiated. This wetting agent solution is formed by mixing 0.06 kg of polysorbate 80 with 6 kg of water and is sprayed at a rate of 1 to 2 kg per minute. After completing the spraying of the polysorbate solution, the fluidizing operation is continued until a moisture level of about 2.0 wt % has been reached. The contents of the bowl are discharged into a siever/shaker (Sweco) equipped with a U.S. Standard 16 mesh screen to remove oversized agglomerates. The sieved material is then transferred into a blender in which 0.06 kg of sieved fumed silica (AEROSIL 200; Degussa AG) is added and blended to form a free flowing particulate ibuprofen-containing granular composition capable of being directly molded into a pharmaceutically-acceptable solid dosage form having high hardness, short disintegration time and fast dissolution rate. Table 1 summarizes the composition of these granules.

TABLE 1

| Ingredients | Amounts, wt % |
| --- | --- |
| Ibuprofen 40 | 90 |
| Sodium Starch Glycolate | 2 |
| Pregelatinized Starch | 7.96 |
| Polysorbate 80 | 0.02 |
| Fumed Silica | 0.02 |

The physical characteristics of the granules are summarized in Table 2.

TABLE 2

| Physical Characteristics | Values | |
| --- | --- | --- |
| Flodex | 4-10 | mm |
| Loose bulk density | 0.45-0.55 | g/mL |
| Tapped bulk density | 0.5-0.65 | g/mL |
| Mean particle size | 200-500 | microns |
| Particles >20 mesh | <2 | wt % |
| Particles <200 mesh | <20 | wt % |

The Flodex values reported in Table 2 illustrate the excellent flow properties of the granules of this invention. These Flodex values are determined by use of a flow measurement instrument manufactured by Hanson Research Incorporated. The value in units of millimeter represents the smallest circular orifice through which the granules may flow starting at the stationary state.

EXAMPLE 2

Preparation of Solid Dosage Forms of the Invention

To illustrate the advantageous properties of the granules of this invention in forming solid dosage forms, two formulations were prepared and evaluated. One such formulation was prepared using the granules produced as in Example 1. The other formulation was prepared in the same manner but using ibuprofen powder having a mean particle size of 70 microns together with other components in amounts designed to provide formulations with acceptable performance in a tablet press.

The composition of the respective formulations used in forming the solid dosage forms is shown in Table 3.

TABLE 3

| Ingredients | Composition of the Invention | Comparable Comparative Composition |
| --- | --- | --- |
| Ibuprofen granules (from Example 1) | 97.78 wt % | — |
| Ibuprofen 70 micron grade (Albemarle Corporation) | — | 88 wt % |
| Microcrystalline cellulose, Avicel PH 102 (FMC) | 1.95 wt % | — |
| SMCC 90 | — | 8.65 wt % |
| Aerosil 200 | 0.02 wt % | 0.5 wt % |
| Sodium croscarmellose | — | 2.5 wt % |
| Magnesium stearate | 0.25 wt % | 0.40 wt % |

Caplets were produced from each of the respective formulations of Table 3 by blending the components of the respective formulations in a suitable blender in order to form homogeneous mixtures of the two formulations under test. This was done by charging all ingredients (sieved through a U.S. Standard 20 mesh sieve) other than magnesium stearate into a two cubic foot twin shell blender (Patterson and Kelly) and blended for 10 minutes. The magnesium stearate (also sieved through a U.S. Standard 20 mesh sieve) was then added to the blender and the mixture was blended for an additional 5 minutes. The respective formulations were then compressed in a 10-station rotary tableting press. The resultant caplets were then subjected to evaluations in order to assess various properties of the respective caplets. Although the dissolution times and hardness of the respective solid dosage forms were comparable, the results of these tests showed that the solid dosage forms of this invention had substantially greater friability resistence than the comparative dosage forms. In particular, using a Distek Friabulator model DF-3 for 20 tablets and 200 revolutions, it was found that the solid dosage forms of this invention having a hardness in the range of 9-15 kPa had a friability of 0.19-0.21 wt %, whereas the comparative solid dosage forms not of this invention, but of the same hardness range, had a friability of 0.40-0.72 wt %.

EXAMPLE 3

Preparation of Solid Dosage Forms of the Invention

Using the blending procedure as described in Example 2, three formulations were prepared. One of these formulations—a formulation of this invention—was made from the granules produced as in Example 1. Another of these formulations (Formulation A) was made in which the ibuprofen was in powder form having a mean particle size of 70 microns (Albemarle Corporation). The third formulation (Formulation B) was made using ibuprofen having a mean particle size of 90 microns (Shangdon Xinhua). Solid dosage forms were produced from each of these formulations using the procedure as described in Example 2, but with the ingredients and proportions set forth in Table 4.

TABLE 4

| Ingredients | Formulation of the invention | Comparative Formulation A | Comparative Formulation B |
|---|---|---|---|
| Ibuprofen granules (from Example 1) | 74.07 wt % | — | — |
| Ibuprofen 70 micron grade (Albemarle Corporation) | — | 66.67 wt % | — |
| Ibuprofen 90 micron grade (Shangdon Xinhua) | — | — | 66.67 wt % |
| Microcrystalline cellulose, Avicel PH 102 (FMC) | 13.33 wt % | 13.33 wt % | 13.33 wt % |
| Pregelatinized starch | 2.16 wt % | 8.08 wt % | 8.08 wt % |
| Fumed silica, CAB-O-SIL | 0.92 wt % | 0.92 wt % | 0.92 wt % |
| Precipitated silica, Syloid 244 (Grace Davison) | 0.58 wt % | 0.58 wt % | 0.58 wt % |
| Plasdone, K 90 | 1.42 wt % | 1.42 wt % | 1.42 wt % |
| Sodium croscarmellose | 3.83 wt % | 3.83 wt % | 3.83 wt % |
| Sodium starch glycolate | 0.69 wt % | 2.17 wt % | 2.17 wt % |
| Stearic acid | 3.00 wt % | 3.00 wt % | 3.00 wt % |
| Total % | 100.00 wt % | 100.00 wt % | 100.00 wt % |

Flodex measurements on the formulated blends of Table 4 showed that the composition of this invention gave a Flodex value of 4 mm. In contrast the Flodex value for Formulation A was 9 mm and the Flodex value for Formulation B was 8 mm.

Solid dosage forms were produced from the formulations of Table 4 as in Example 2 using a series of compression forces and then measuring the ejection force, caplet hardness, and caplet friability. The results of these evaluations are summarized in Table 5.

TABLE 5

| | Compression Force, metric tons | Ejection Force, kg | Hardness, kPa | Friability after 200 revolutions, wt % | Friability after 400 revolutions, wt % |
|---|---|---|---|---|---|
| Formulation of the Invention | 1.58 | 114 | 8.7 | 0.18 | 0.43 |
| | 2.04 | 125 | 12.6 | 0.16 | 0.32 |
| | 2.65 | 134 | 15.4 | 0.16 | 0.24 |
| | 3.34 | 138 | 17.7 | 0.13 | 0.24 |
| | 3.64 | 144 | 18.7 | — | — |
| Formulation A | 1.38 | 123 | 5.2 | 2.81 | 7.75 |
| | 1.65 | 131 | 6.2 | 1.36 | 3.74 |
| | 2.03 | 136 | 7.8 | 0.39 | 1.56 |
| | 2.39 | 138 | 9.2 | 0.31 | 0.78 |
| | 3.05 | 145 | 11.5 | 0.27 | 0.52 |
| Formulation B | 1.87 | 156 | 8.6 | 0.86 | 2.76 |
| | 2.04 | 163 | 10.1 | 0.46 | 1.70 |
| | 2.63 | 184 | 12.7 | 0.35 | 0.71 |
| | 3.59 | 198 | 14.6 | 0.28 | 0.57 |

It can be seen from the results of Table 5 that the solid dosage forms of this invention had superior properties for any given force. Especially noteworthy are the friability results. Another advantageous feature of this invention is the excellent weight uniformity of individual solid dosage units. For example, weight measurements on 10 dosage units from each of the solid dosage units of this invention in Examples 1-3 were well within the strict tolerance levels promulgated by the United States Pharmacopia (USP).

Still another advantageous feature of this invention is the fact that the granule possesses a super disintegrant which is substantially uniformly dispersed within the granule and this in turn enables the production of solid dosage forms in which a super disintegrant is present and substantially uniformly dispersed both in the granules and in the other solids used in forming the solid dosage form. In other words, the resultant solid dosage form has at least one pharmaceutically-acceptable super disintegrant substantially uniformly dispersed throughout the composition (i.e., the super disintegrant is substantially uniformly dispersed both intragranularly and extragranularly). Such substantially uniform dispersal of the super disintegrant results in the ibuprofen (and any other active pharmaceutically-active component that may be associated therewith) to rapidly go into solution upon addition of the solid dosage form to water. The extragranularly uniformly dispersed super disintegrant causes the solid dosage form to rapidly break up and concurrently the intragranularly uniformly dispersed super disintegrant causes the granules to rapidly break up thereby liberating the ibuprofen which in turn is rapidly dissolved in the water.

EXAMPLE 4

In order to demonstrate the substantially uniform dispersal of the super disintegrant in the granules of this invention, the following experimental work was performed. A granule was produced following the steps described hereinabove. The granule consisted of 90 wt % ibuprofen, 7.98 wt % starch (WG 220 by National Starch), 2.0 wt % Na starch glycolate (Explotab low pH), and 0.02 wt % polysorbate 80 (Tween 80). A 100 gram sample was placed in a mechanical sieve stack consisting 20, 40, 60, 80, and 200 mesh screens. The sample was sieved for 20 minutes and the results of the sieving were as set forth in Table 6.

TABLE 6

| Sieve Screen Size | Sieve retention, grams | Na Concentration, ppm |
|---|---|---|
| 20 mesh | 0.39 | NA |
| 40 mesh | 12.65 | 999 |
| 60 mesh | 31.8 | 1030 |
| 80 mesh | 23.74 | 1130 |
| 200 mesh | 17.93 | 1325 |
| Average | | 1121 |
| STDEV | | 147 |
| RSTD | | 13.1% |

The amount of material retained on each sieve screen is given in column 2 and Na contents as measured by ICP is given in Column 3. The Na content in the ibuprofen is only a few ppm, the Na content in WG 220 is about 150 ppm. Thus, the majority of the Na comes from the super disintegrant, sodium starch glycolate. Thus, to monitor the Na content in various size fractions is a good method in determining the distribution of sodium starch glycolate. The Na concentrations determined from various size fraction indicate that Na starch glycolate is well distributed in all size fractions. An average of 1121 ppm, standard deviation of 147 ppm and relative standard deviation of 13.1% are obtained Na contents determined in all size fractions. This kind of Na distribution will never occur if Na starch glycolate were blended into much larger ibuprofen granules. In this connection, the Na starch glycolate has basically no particles greater than 200 mesh in size and therefore should be removed by sieving.

The following work demonstrates not only that Na starch glycolate is substantially distributed evenly in various size fractions, but also is substantially evenly distributed in and on each granular particle. Scanning Electron Microscopy with Energy Dispersive X-ray Analysis (SEM/EDX) technique was used to show presence of sodium (from sodium starch glycolate) on granules of ibuprofen. A JOEL JSM-6300F field-emission type scanning electron microscope was used. An Oxford Instruments Model 6731 X-ray detector with INCA microanalysis software was used for generation of element maps. A sample from each size fraction was coated with a thin film of carbon with Bal-Tec CED-30 carbon evaporator. An electron beam was generated at 20 KV and X-rays were collected for extended periods required for mapping. An x-ray spectrum from each of the size fractions indicated the presence of sodium in the granules. Sodium maps also showed sodium to be present in each granule. The maps tend to indicate that sodium (and sodium starch glycolate) is present in a substantially uniform manner in the granules.

It is to be understood that the ingredients referred to by chemical name or formula anywhere in the specification or claims hereof, whether referred to in the singular or plural, are identified as they exist prior to coming into contact with another substance referred to by chemical name or chemical type (e.g., another reactant, a solvent, a diluent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and other materials are identified as ingredients to be brought together in connection with performing a desired chemical reaction or in forming a mixture to be used in conducting a desired reaction. Also, even though the claims hereinafter may refer to substances, components and/or ingredients in the present tense ("comprises", "is", etc.), the reference is to the substance or ingredient as it existed at the time just before it was first contacted, blended or mixed with one or more other substances or ingredients in accordance with the present disclosure. The fact that the substance or ingredient may have lost its original identity through a chemical reaction or transformation or complex formation or assumption of some other chemical form during the course of such contacting, blending or mixing operations, is thus wholly immaterial for an accurate understanding and appreciation of this disclosure and the claims thereof. Nor does reference to an ingredient by chemical name or formula exclude the possibility that during the desired reaction itself an ingredient becomes transformed to one or more transitory intermediates that actually enter into or otherwise participate in the reaction. In short, no representation is made or is to be inferred that the named ingredients must participate in the reaction while in their original chemical composition, structure or form.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise. As used herein, the terms "appreciable" and "appreciably" mean sufficient to be readily perceived and more than a mere trace or insignificant amount, but less than an unacceptable substantial amount. Similarly, the term "substantially uniformly" means that the substance is dispersed sufficiently within the body of the granules as to enable more rapid breakup of the granules in water than if the substance was not present in the granules.

This invention is susceptible to considerable variation in its practice.

That which is claimed is:

1. Pharmaceutical granules consisting of (i) 75 wt % or more of ibuprofen, (ii) in the range of about 0.5 to about 10 wt % of sodium starch glycolate, (iii) in the range of about 2 to about 14.5 wt % of at least one pharmaceutically-acceptable binder, which binder is different from sodium starch glycolate, (iv) in the range of about 0.01 to about 2.0 wt % of at least one pharmaceutically-acceptable wetting agent, and optionally (v) in the range of about 0.01 to about 0.5 wt % of at least one pharmaceutically-acceptable glidant, and (vi) a moisture content that is less than 5 wt %, wherein sodium starch glycolate is substantially uniformly dispersed in the granules, wherein said granules are devoid of non-crosslinked polyvinylpyrrolidone, wherein said wetting agent remains on the outer surface of said granules, wherein the foregoing percentages of (i), (ii), (iii), (iv), and (v) are based on the dry weight of said granules, and the weight of (vi) is based on the weight of the granules, and wherein said granules are formed by spraying an aqueous solution, dispersion, or suspension of (iii), followed by spraying an aqueous solution, dispersion, or suspension of (iv), onto a fluidized mixture of (i) and (ii).

2. Pharmaceutical granules as in claim 1 wherein the amount of ibuprofen in the granules is in the range of about 85 to about 95 wt %, the amount of sodium starch glycolate in the granules is in the range of about 0.5 to about 10 wt %, and wherein the amount of said at least one pharmaceutically-acceptable binder in the granules is in the range of about 5 to about 10 wt %, all of the foregoing percentages being based on the dry weight of said granules, and wherein said granules have a moisture content that is less than 2 wt %, based on the weight of the granules.

3. Pharmaceutical granules as in claim 2 wherein at least one pharmaceutically-acceptable glidant is present in said granules in an amount in the range of about 0.01 to about 0.1 wt %, with the proviso that when the glidant is fumed silica the amount thereof is in the range of about 0.01 to about 0.05 wt %, wherein the foregoing weight percentages are based on the dry weight of said granules.

4. Pharmaceutical granules as in claim 2 wherein the amount of sodium starch glycolate in the granules is an amount in the range of about 1 to about 5 wt % based on the dry weight of said granules.

5. A process of preparing granules according to claim 1 enriched in ibuprofen and devoid of non-crosslinked polyvinylpyrrolidone, which process comprises the steps of:
  a) forming a mixture from, or obtaining a mixture of, finely-divided ibuprofen and finely-divided sodium starch glycolate;
  b) fluidizing mixture from a) with gaseous fluidizing agent to thereby form a substantially homogeneous dry mixture comprised of ibuprofen and sodium starch glycolate;
  c) while fluidizing homogeneous dry mixture formed in b) with heated gaseous fluidizing agent, spraying onto the fluidized mixture an aqueous solution, dispersion, or suspension of at least one pharmaceutically-acceptable binder which is different from sodium starch glycolate, followed by an aqueous solution, dispersion, or suspension of at least one pharmaceutically-acceptable wetting agent, to form wet granules consisting of (1) ibuprofen, (2) sodium starch glycolate, (3) at least one pharmaceutically-acceptable binder which is different from sodium starch glycolate, (4) water, and (5) at least one pharmaceutically-acceptable wetting agent, said wet granules being devoid of non-crosslinked polyvinylpyrrolidone; and
  d) fluidizing wet granules from c) with heated gaseous fluidizing agent so as to produce granules that are devoid of non-crosslinked polyvinylpyrrolidone and that optionally have a moisture content that is less than 5 wt % based on the weight of the granules.

6. A process of claim 5 wherein the respective amounts of the finely-divided ibuprofen, the sodium starch glycolate used, and the at least one pharmaceutically-acceptable binder used are proportioned to provide granules consisting of (i) in the range of about 85 to about 95 wt % of ibuprofen (ii) in range of about 1 to about 5 wt % of sodium starch glycolate, (iii) in the range of about 2 to about 14.5 wt % of the at least one binder and (iv) in the range of about 0.01 to about 2.0 wt % of the at least one pharmaceutically-acceptable wetting agent, wherein all of the foregoing percentages are based on the dry weight of the granules, and wherein the granules produced in d) have a moisture content that is less than 2 wt % based on the weight of the granules.

7. A process as in claim 6 wherein the respective fluidizing in b), c), and d) are conducted at temperatures which are independently in the range of 20-80° C.

8. A process as in claim 7 wherein the fluidizing inlet air temperature in c) maintains a fluidized bed moisture content in the range of 12 to 20 wt % for at least 20 minutes.

9. A process as in claim 5 wherein the fluidizing inlet air temperature in c) maintains a fluidized bed moisture content in the range of 17 to 20 wt % for a period of time in the range of 30 to 60 minutes.

10. A process as in claim 5 further comprising the step of adding at least one glidant to granules dried as in d), and physically mixing the glidant with said granules without appreciably breaking down the structure of said granules, so that said granules consist of ibuprofen, sodium starch glycolate, at least one pharmaceutically-acceptable binder, which is different from sodium starch glycolate, at least one pharmaceutically-acceptable wetting agent, and at least one glidant, and wherein the granules produced in d) have a moisture content that is less than 2 wt % based on the weight of the granules.

11. A process as in claim 10 wherein said glidant is at least one powdery silica glidant and wherein the amount thereof used is in the range of 0.01 to 0.1 wt % based on the weight of the final silica glidant treated product.

12. A process as in claim 5 wherein
  1) d) is conducted to produce granules having a moisture content that is less than 2 wt % based on the weight of the granules;
  2) said respective amounts used produce granules containing in the range of 1 to 5 wt % of sodium starch glycolate, and in the range of 5 to 10 wt % of said at least one pharmaceutically-acceptable binder, the foregoing weight percentages each being based on the dry weight of the granules;
  3) the respective fluidizing in b), c), and d) are conducted at temperatures which are independently in the range of 20-80° C.;
  4) the fluidizing inlet air temperature in c) maintains a fluidized bed moisture content in the range of 12 to 20 wt % for at least 20 minutes;
  5) c) is conducted by spraying onto the fluidized mixture separately (i) said aqueous solution, dispersion, or suspension of at least one pharmaceutically-acceptable binder and (ii) an aqueous solution, dispersion, or suspension of at least one pharmaceutically-acceptable wetting agent, to form wet granules; and
  6) said respective amounts used produce granules which additionally contain in the range of about 0.01 to about 2.0 wt % of said at least one pharmaceutically-acceptable wetting agent based on the dry weight of the granules.

13. A process as in claim 12 wherein the respective fluidizing in b), c), and d) are conducted at temperatures which are independently in the range of 50 to 80° C.

14. A process as in claim 12 wherein the fluidizing inlet air temperature in c) maintains a fluidized bed moisture content in the range of 17 to 20 wt % for a period of time in the range of 30 to 60 minutes.

15. A process as in claim 12 further comprising adding a glidant to granules dried as in d), and physically mixing the glidant with said granules without appreciably breaking down the structure of said granules.

16. A process as in claim 15 wherein said glidant is at least one powdery silica glidant and wherein the amount thereof used is in the range of 0.01 to 0.1 wt % based on the weight of the final silica glidant treated product.

17. A method of preparing a pharmaceutical dosage form, which method comprises filling capsules with pharmaceutical granules of claim 1.

18. A pharmaceutical dosage form comprised of
  A) capsules at least partially filled with pharmaceutical granules which granules have been dried to a moisture content that is less than 5 wt % and having a glidant physically mixed therewith, or
  B) compressed solid dosage forms produced using pharmaceutical granules which granules have been dried to a moisture content that is less than 5 wt % and having a glidant physically mixed therewith;

said pharmaceutical granules consisting of (i) 75 wt % or more of ibuprofen, (ii) in the range of about 0.5 to about 10 wt % of sodium starch glycolate and (iii) in the range of about 2 to about 14.5 wt % of at least one pharmaceutically-acceptable binder, which binder is different from sodium starch glycolate, (iv) in the range of about 0.01 to about 2.0 wt % of at least one pharmaceutically-acceptable wetting agent, and optionally (v) in the range of about 0.01 to about 0.5 wt % of at least one pharmaceutically-acceptable glidant, and (vi) a moisture content that is less than 5 wt %, wherein sodium starch glycolate is substantially uniformly dispersed in said granules, wherein said granules are devoid of non-crosslinked polyvinylpyrrolidone, wherein said wetting agent remains on the outer surface of said granules, and wherein the foregoing percentages of (i), (ii), (iii), (iv), and (v) are based on the dry weight of said granules, and the weight of (vi) is based on the weight of the granules, and wherein said granules are formed by spraying an aqueous solution, dispersion, or suspension of (iii), followed by spraying an aqueous solution, dispersion, or suspension of (iv), onto a fluidized mixture of (i) and (ii).

19. Pharmaceutical granules as in claim 1 wherein said at least one pharmaceutically-acceptable binder used in forming the granules is pregelatinized starch, said at least one pharmaceutically-acceptable wetting agent is used in forming the granules and as used in forming the granules is polyoxyethylene 20-sorbitan monooleate, and said at least one pharmaceutically-acceptable glidant is used in forming the granules and as used in forming the granules is fumed silica.

20. Pharmaceutical granules as in claim 19 wherein the ingredients of the granules are proportioned to provide granules having the following composition: ibuprofen, 90 wt %; sodium starch glycolate, 2 wt %; pregelatinized starch, 7.96 wt %; polyoxyethylene 20-sorbitan monooleate, 0.02 wt %; and fumed silica, 0.02 wt %, wherein the foregoing percentages are based on the dry weight of said granules, and wherein the moisture content that is less than 5 wt % based on the weight of the granules.

21. Pharmaceutical granules as in claim 20 wherein the granules have the following physical characteristics: a Flodex value in the range of 4 to 10 millimeters, a loose bulk density in the range of 0.45 to 0.55 g/mL, a tapped bulk density of 0.5 to 0.65 g/mL, a mean particle size in the range of 200 to 500 microns, less than 2 wt % of particles that are greater than 20 mesh size, and less than 20 wt % of particles that are less than 200 mesh size.

22. Pharmaceutical granules as in claim 1 sized to pass through a standard number 16 mesh sieve and be retained on a U.S. standard number 200 mesh sieve.

23. Pharmaceutical granules as in claim 1 wherein said binder is on said granules such that the sodium starch glycolate remains substantially uniformly dispersed.

* * * * *